United States Patent
Mohedas et al.

(10) Patent No.: US 7,232,848 B2
(45) Date of Patent: Jun. 19, 2007

(54) GAS AGITATED MULTIPHASE REACTOR WITH STATIONARY CATALYST SOLID PHASE

(75) Inventors: Sergio R. Mohedas, Ponca City, OK (US); Rafael L. Espinoza, Ponca City, OK (US); Jianping Zhang, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 551 days.

(21) Appl. No.: 10/238,008

(22) Filed: Sep. 9, 2002

(65) Prior Publication Data

US 2004/0048938 A1  Mar. 11, 2004

(51) Int. Cl.
*C07C 27/26* (2006.01)
*B01J 8/04* (2006.01)

(52) U.S. Cl. .................. 518/726; 518/700; 518/706; 518/715; 422/173; 422/177; 422/180; 422/188; 422/197; 422/198; 422/211; 422/222; 422/238; 422/239; 208/59; 208/89; 208/107; 208/212; 585/440; 585/700

(58) Field of Classification Search ............... 422/173, 422/177, 180, 198, 211, 222, 188, 197, 238, 422/239; 208/59, 89, 93, 107, 212; 518/700, 518/706, 715, 726; 585/440, 700
See application file for complete search history.

(56) References Cited

U.S. PATENT DOCUMENTS

| 2,448,279 A | 8/1948 | Rubin |
| 2,560,171 A | 7/1951 | Hill |
| 2,576,858 A | 11/1951 | Rubin |
| 2,987,465 A | 6/1961 | Johanson |
| 3,663,179 A | 5/1972 | Mehta et al. |
| 3,812,210 A | 5/1974 | Higdon et al. ............... 260/638 |
| 4,196,100 A | 4/1980 | Pargeter et al. ............. 252/439 |
| 4,252,736 A | 2/1981 | Haag et al. .................. 260/450 |
| 4,279,830 A | 7/1981 | Haag et al. .................. 518/700 |
| 4,312,741 A | 1/1982 | Jacquin |

(Continued)

FOREIGN PATENT DOCUMENTS

GB  2 204 055  11/1988

(Continued)

OTHER PUBLICATIONS

Schulz et al., Applied Catalyst vol. 186 No. 1, Oct. 2, 1999 (229 p.).

(Continued)

*Primary Examiner*—Glenn Caldarola
*Assistant Examiner*—Prem C. Singh
(74) *Attorney, Agent, or Firm*—Conley Rose P.C.

(57) ABSTRACT

An apparatus for converting a gaseous and/or liquid feed fluid to gaseous and/or liquid products using a solid catalyst comprises a reactor, a liquid phase disposed within the reactor volume, a fixed catalyst at least partially disposed in the liquid phase, a cooling system having a cooling element in thermal contact with the liquid phase, a feed inlet positioned to feed the feed fluid into the reactor volume, and a fluid outlet in fluid communication with the liquid phase. The catalyst is contained in a catalyst container and the container may be adjacent to said cooling element, extend through said cooling element, or may surround the catalyst container. The catalyst may be a Fischer-Tropsch catalyst.

46 Claims, 5 Drawing Sheets

U.S. PATENT DOCUMENTS

| | | | | |
|---|---|---|---|---|
| 4,339,413 A | * | 7/1982 | Lahne et al. | 422/200 |
| 4,397,964 A | | 8/1983 | Pargeter et al. | 518/713 |
| 4,422,961 A | | 12/1983 | Gray | |
| 4,525,482 A | | 6/1985 | Ohsaki et al. | 518/707 |
| 4,937,051 A | | 6/1990 | Graven et al. | 422/194 |
| 5,137,924 A | | 8/1992 | Short et al. | 518/700 |
| 5,177,289 A | | 1/1993 | Smith, Jr. et al. | 585/526 |
| 5,190,730 A | | 3/1993 | Smith, Jr. et al. | 422/109 |
| 5,436,383 A | | 7/1995 | Le Peltier et al. | 585/655 |
| 5,520,890 A | | 5/1996 | Lorentzen et al. | 422/197 |
| 5,712,313 A | | 1/1998 | Kramer et al. | 518/706 |
| 5,756,055 A | | 5/1998 | Kelly et al. | 422/194 |
| 5,776,988 A | * | 7/1998 | Chaumette et al. | 518/715 |
| 5,786,393 A | | 7/1998 | Chaumette et al. | 518/700 |
| 5,792,428 A | | 8/1998 | Bakshi et al. | 422/112 |
| 5,827,903 A | | 10/1998 | White et al. | 518/710 |
| 5,961,933 A | | 10/1999 | Casanave et al. | 422/211 |
| 6,060,524 A | | 5/2000 | Casanave et al. | 518/706 |
| 6,114,400 A | | 9/2000 | Nataraj et al. | 518/715 |
| 6,169,120 B1 | | 1/2001 | Beer | 518/715 |
| 6,190,535 B1 | * | 2/2001 | Kalnes et al. | 208/89 |
| 6,211,255 B1 | | 4/2001 | Schanke et al. | 518/715 |
| 6,225,358 B1 | | 5/2001 | Kennedy | 518/700 |
| 6,239,184 B1 | | 5/2001 | Beer et al. | 518/709 |
| 6,262,131 B1 | * | 7/2001 | Arcuri et al. | 518/700 |
| 6,299,759 B1 | | 10/2001 | Bradway et al. | 208/59 |
| 6,310,108 B1 | | 10/2001 | Bonneau et al. | 518/700 |
| 6,558,634 B1 | * | 5/2003 | Wang et al. | 422/173 |
| 6,660,237 B2 | | 12/2003 | Wang et al. | |
| 2002/0018740 A1 | | 2/2002 | Filippi et al. | |
| 2003/0175184 A1 | | 9/2003 | Filippi et al. | |

FOREIGN PATENT DOCUMENTS

| | | |
|---|---|---|
| WO | WO 94/12274 | 6/1994 |
| WO | WO 00/76652 | 12/2000 |
| WO | WO 00/76653 | 12/2000 |
| WO | WO 03/043727 | 5/2003 |

OTHER PUBLICATIONS

G. Alex Mills, *Status and Future Opportunities for Conversion of Synthesis Gas to Liquid Fuels*, Fuel 1994 vol. 73, No. 8 (pp. 1243-1279).

* cited by examiner

GAS AGITATED MULTIPHASE REACTOR WITH STATIONARY CATALYST SOLID PHASE

RELATED APPLICATIONS

None

STATEMENT REGARDING FEDERALLY SPONSORED RESEARCH OR DEVELOPMENT

Not applicable

TECHNICAL FIELD OF THE INVENTION

The present invention relates to a method and apparatus for converting synthesis gas, i.e., a mixture of carbon monoxide and hydrogen, to hydrocarbons, typically referred to as the Fischer-Tropsch reactions or the Fischer-Tropsch process. More particularly this invention relates to the use of a gas agitated multiphase reactor to achieve both reaction of the syngas and separation of the hydrocarbon product.

BACKGROUND

Large quantities of methane, the main component of natural gas, are available in many areas of the world, and natural gas is predicted to outlast oil reserves by a significant margin. However, most natural gas is situated in areas that are geographically remote from population and industrial centers. The costs of compression, transportation, and storage make its use economically unattractive. To improve the economics of natural gas use, much research has focused on the use of methane as a starting material for the production of higher hydrocarbons and hydrocarbon liquids, which are more easily transported and thus more economical. The conversion of methane to hydrocarbons is typically carried out in two steps. In the first step, methane is converted into a mixture of carbon monoxide and hydrogen (i.e., synthesis gas or syngas). In a second step, the syngas is converted into hydrocarbons.

This second step, the preparation of hydrocarbons from synthesis gas, is well known in the art and is usually referred to as Fischer-Tropsch synthesis, the Fischer-Tropsch process, or Fischer-Tropsch reaction(s). Fischer-Tropsch synthesis generally entails contacting a stream of synthesis gas with a catalyst under temperature and pressure conditions that allow the synthesis gas to react and form hydrocarbons.

More specifically, the Fischer-Tropsch reaction entails the catalytic hydrogenation of carbon monoxide to produce any of a variety of products ranging from methane to higher alkanes and aliphatic alcohols. The reaction is carried out by contacting the hydrogen and carbon monoxide with a catalyst. The reaction gives off a large amount of heat. When the Fischer-Tropsch reaction is carried out in fixed-bed reactors, this high heat of reaction results in an increase in the temperature of the catalyst bed above that of the surrounding environment. Excessive temperature rises can lead to inferior product distribution, and can damage the catalyst if not controlled.

When the Fischer-Tropsch process is carried out in a fixed bed reactor, synthesis gas is fed via an inlet into direct contact with a catalyst located inside catalyst tubes, while heat is removed from the catalyst bed through catalyst tube walls to a heat exchange medium outside the catalyst tubes. The heat exchange medium may be water. As previously described, the catalyst is typically contained in one or more tubular conduits and the heat exchange medium is located in the spaces between the catalyst tubes. The optimum temperature gradient between the catalyst and the heat exchange medium must be such that the catalyst produces a product having the desired spectrum of hydrocarbons while the catalyst bed remains thermally stable.

Slurry bed reactors allow operators to maintain a more uniform temperature profile along both axial and radial directions of the reactors than those of fixed bed reactors. Also, in slurry bed reactors the heat transfer properties are better than in fixed bed reactors, which leads to better temperature control, an important parameter for exothermic reactions (i.e. Fischer-Tropsch reactions).

The hydrocarbons produced in the Fischer-Tropsch process range from single-carbon methane gas, up to $C_{50}$ and higher. Because some of the produced hydrocarbons are liquids at the Fischer-Tropsch reactor conditions, there is a need to continuously remove the product from the reactor by separating the liquid from the solid catalyst particles in the slurry. This operation is difficult and expensive to implement. Furthermore, during the separation process, there is a high probability of catalyst attrition, which, in turn, is detrimental to the separation process and may cause loss of catalyst from the reactor and contamination of the products, with negative effects for the processes downstream from the Fischer-Tropsch reactor.

Hence, there remains a need for a catalyst system that provides good heat transfer and thermal control capabilities while minimizing catalyst attrition and avoiding the need for liquid/solid separation equipment.

SUMMARY OF THE INVENTION

The present catalyst system provides good heat transfer and thermal control capabilities while minimizing catalyst attrition and avoiding the need for liquid/solid separation equipment. The present invention avoids catalyst attrition by containing the solid catalyst particles within containers, which are immersed in the gas-liquid mixture of reactants and products. Also, by containing the catalyst, the removal of the liquid products can be performed without the need for a solid-liquid separation process.

By utilizing a stationary catalyst phase inside a multiphase reactor, the present system provides the advantage of better heat transfer properties and a more uniform temperature in the reactor than those that are achieved in conventional fixed bed systems and avoids the need for costly separation process of solids (catalyst) and liquid to remove the portion of the products from the reactor that are liquid at typical Fischer-Tropsch operating conditions, as is necessary in conventional slurry bed systems. In addition, the present invention is applicable to any Gas-to-Liquids reactions that are catalyzed by solid catalysts, such as Fischer-Tropsch reactions, wax hydroprocessing, or oxygenate synthesis reactions (i.e. alcohol synthesis) or wax hydrotreating or wax hydrocracking and/or hydroisomerization or unsaturated hydrocarbon synthesis reactions.

In a preferred embodiment of the present invention, a method for converting a feed to a product includes providing a stationary catalyst phase having a catalyst inside a multiphase reactor and contacting a feed stream with the catalyst so as to produce a gas and/or liquid product.

In one preferred embodiment, the present invention comprises a reactor for converting a gaseous feed to liquid products using a solid catalyst. The reactor contains a liquid phase disposed therein, a fixed catalyst at least partially disposed in said liquid phase, and a cooling system having a cooling element in thermal contact with said liquid phase. A feed gas inlet is positioned to feed the gaseous feed into said reactor and a fluid outlet in fluid communication with the liquid phase allows for removal of fluids from the reactor. The fixed catalyst and the cooling system can be positioned in various configurations in the reactor. For example, the catalyst can be contained in a catalyst container that is adjacent to said cooling element or extends through the cooling element, or the cooling element can extend through the catalyst container. Alternatively, the catalyst can be affixed to an outer surface of said cooling element. The catalyst container can be porous, and the catalyst may or may not be particulate or monolithic. In particularly preferred embodiments, the catalyst is a Fischer-Tropsch catalyst, an oxygenates producing catalyst, or wax hydrotreating or wax hydrocracking and/or hydroisomerization or unsaturated hydrocarbon synthesis reactions.

In yet another preferred embodiment of the present invention, an apparatus for converting gaseous and/or liquid reactants to gaseous and/or liquid products includes a multiphase reactor having a stationary catalyst phase, a feed line for providing a reactant feed to the reactor, a liquid output line for receiving liquid product from the reactor, and a gas output line for receiving gas product and un-reacted gas feed from the reactor. In some embodiments, the reactant feed comprises synthesis gas. In other embodiments the reactant feed comprises hydrogen rich gas and liquid hydrocarbon or waxes. The stationary catalyst phase preferably includes a catalyst active for converting synthesis gas to hydrocarbons, such as a Fischer-Tropsch catalyst. In other embodiments the stationary catalyst phase includes a catalyst active for alcohols synthesis or unsaturated hydrocarbons synthesis reactions or hydrotreating or hydrocracking or hydroisomerization of hydrocarbons or waxes.

BRIEF DESCRIPTION OF THE DRAWINGS

A better understanding of the present invention can be obtained when the following detailed description of the preferred embodiment is considered in conjunction with the drawings, wherein.

DETAILED DESCRIPTION OF THE PREFERRED EMBODIMENTS

While the present invention is described below in the context of a Fischer-Tropsch system, it will be understood that the devices and principles disclosed herein are equally applicable to any gas-to-liquids operation that uses a solid catalyst.

Reactor

As explained above, the present system provides the advantage of better heat transfer properties and a more uniform temperature in the reactor than in fixed bed reactors while avoiding the need for costly separation process of solids (catalyst) and liquid to remove the portion of the products from the reactor that are liquid at typical Fischer-Tropsch operating conditions by utilizing a stationary catalyst phase inside a multiphase reactor.

Figure 1:
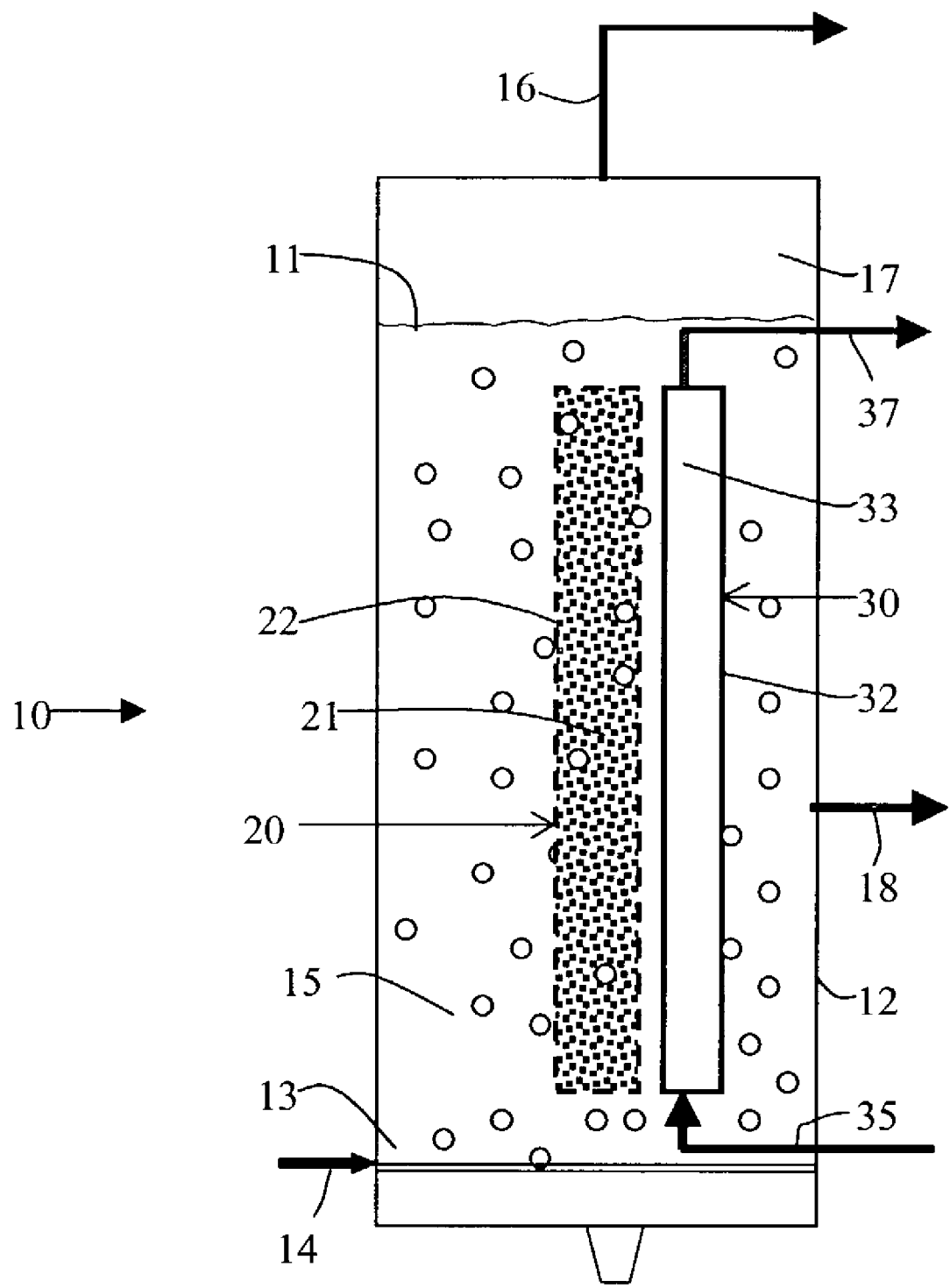
FIG. 1 is a schematic illustration of a reactor system constructed in accordance with a first embodiment of the present invention.

Referring initially to FIG. 1, one embodiment of the present system comprises a reactor 10 that includes reactor housing 12 and a catalyst container 20. In the preferred embodiment shown, catalyst container 20 is cylindrical, but it will be understood that catalyst container 20 may be any shape. Catalyst container 20 comprises a catalyst retainer or outer wall 22, which preferably comprises a tubular member and defines a lumen 21. The volume between catalyst container 20 and reactor housing 12 defines a reaction chamber 15 and is filled with a gas and liquid phase 11.

Lumen 21 is preferably packed with a suitable Fischer-Tropsch catalyst system, which may comprise a supported or unsupported Fischer-Tropsch catalyst. In some embodiments, the catalyst is provided in the form of a monolith or a plurality of distinct or discrete structures or particulates. The terms "distinct" or "discrete" structures or units, as used herein, refer to supports in the form of agglomerated or divided materials such as granules, beads, pills, pellets, cylinders, trilobes, extrudates, spheres, particles formed using spray dried techniques or other rounded shapes or agglomerates of these forms, or another manufactured configuration. Alternatively, the divided material may be in the form of irregularly shaped particles. The term "monolith" as used herein refers to any singular piece of material of continuous manufacture such as solid pieces of metal or metal oxide or foam materials or honeycomb structures.

Outer wall 22 of catalyst container 20 is preferably porous or comprises mesh or the like, so as to allow the easy passage therethrough of gas and liquid while still containing the catalyst. In a preferred embodiment, outer wall 22 is constructed from sintered metal, woven wire mesh metal, sintered wire cloth sheets, perforated metal sheets or wedge wire type materials or the like.

Reactor 10 further includes a feed gas and/or liquid inlet line 14, a gas outlet line 16 and a liquid outlet line 18. Alternatively gas and liquid feeds may be separate. Inlet line 14, containing gas and/or liquid, opens into lower end 13 of reaction chamber 15. Gas outlet line 16 and liquid outlet line 18 each preferably communicate with reaction chamber 15. Inlet 14 and outlets 16, 18 may comprise nozzles (not shown) or any other type of vents that direct gas/liquid into/away from reactor 10. In addition, inlet line 14 and outlets lines 16, 18 may be located at one or more locations in the reactor.

Still referring to FIG. 1, reactor 10 preferably includes a cooling system 30 that includes a cooling element in direct or indirect thermal contact with the liquid in the reactor. In a preferred embodiment, the cooling element comprises at least one cooling tube 32 in direct thermal contact with liquid phase. In the embodiment shown in FIG. 1, cooling tube 32 passes through reaction chamber 15 but does not directly contact catalyst container 20. Cooling tube 32 can comprise a tube having a fluid passage 33 that extends from the lower end 13 of reaction chamber 15 to the upper end 17 of reaction chamber 15, as shown, or can be any other suitable configuration that is suitable for effective heat exchange between the cooling system and the contents of chamber 15 (e.g. a coiled tube that spirals around the circumference of chamber 15). A cooling medium, such as water, enters cooling tube 32 via inlet coolant line 35 and exits via coolant outlet line 37 after absorbing and removing heat from chamber 15. The heated medium can be used as a heat source in another system, or simply cooled and recycled. It will be understood that cooling system 30 can take other forms, including any suitable heat-removal device capable of removing heat from the system without interfering with the catalytic reaction, including but not limited to multiple tubes passing through reaction chamber 15.

Figure 2:
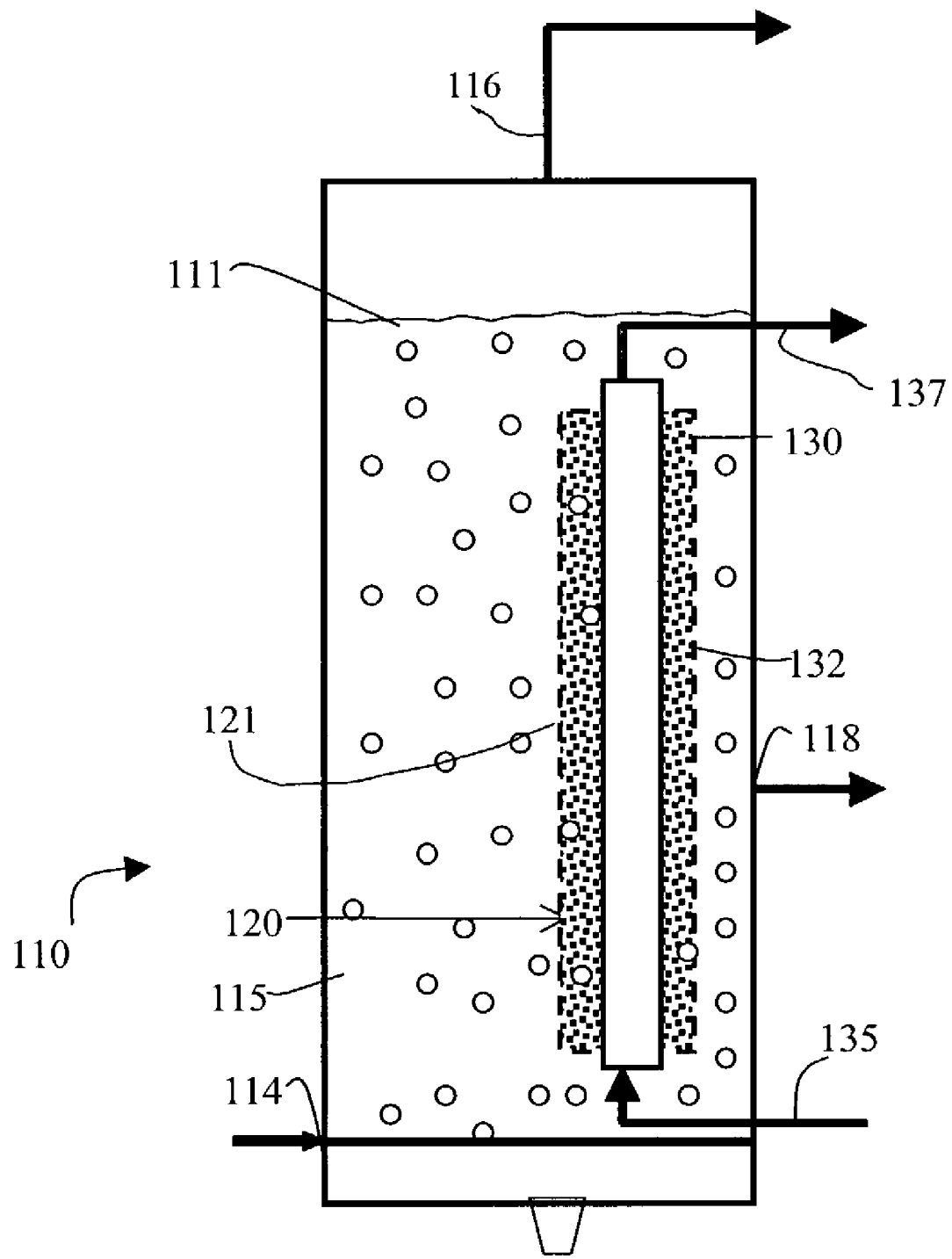
FIG. 2 is a schematic illustration of a reactor system constructed in accordance with a second embodiment of the present invention.

Referring now to FIG. 2, a second embodiment comprising a reactor 110 includes a catalyst container 120 combined with a cooling system 130. Gas and liquid phase 111 is contained in reaction chamber 115. Cooling system 130 includes a cooling tube 132 having an inlet 135 and an outlet 137. In this embodiment, cooling tube 132 is preferably positioned so that it passes through catalyst container 120. In one preferred embodiment cooling tube 132 and catalyst container 120 are concentric, with catalyst container 120 having a diameter larger than that of cooling tube 132, so that an annulus 121 is defined therebetween. In a preferred embodiment, cooling tube 132 is used to remove heat from reactor 110 by circulating and vaporizing the cooling medium, while annulus 121 contains the catalyst particles. Cooling tube 132 preferably has solid walls, while the catalyst container 120, like catalyst container 20 above, preferably has perforated walls constructed from sintered metal, woven wire mesh metal, sintered wire cloth sheets, perforated metal sheets or wedge wire type materials.

Figures 3, 4:
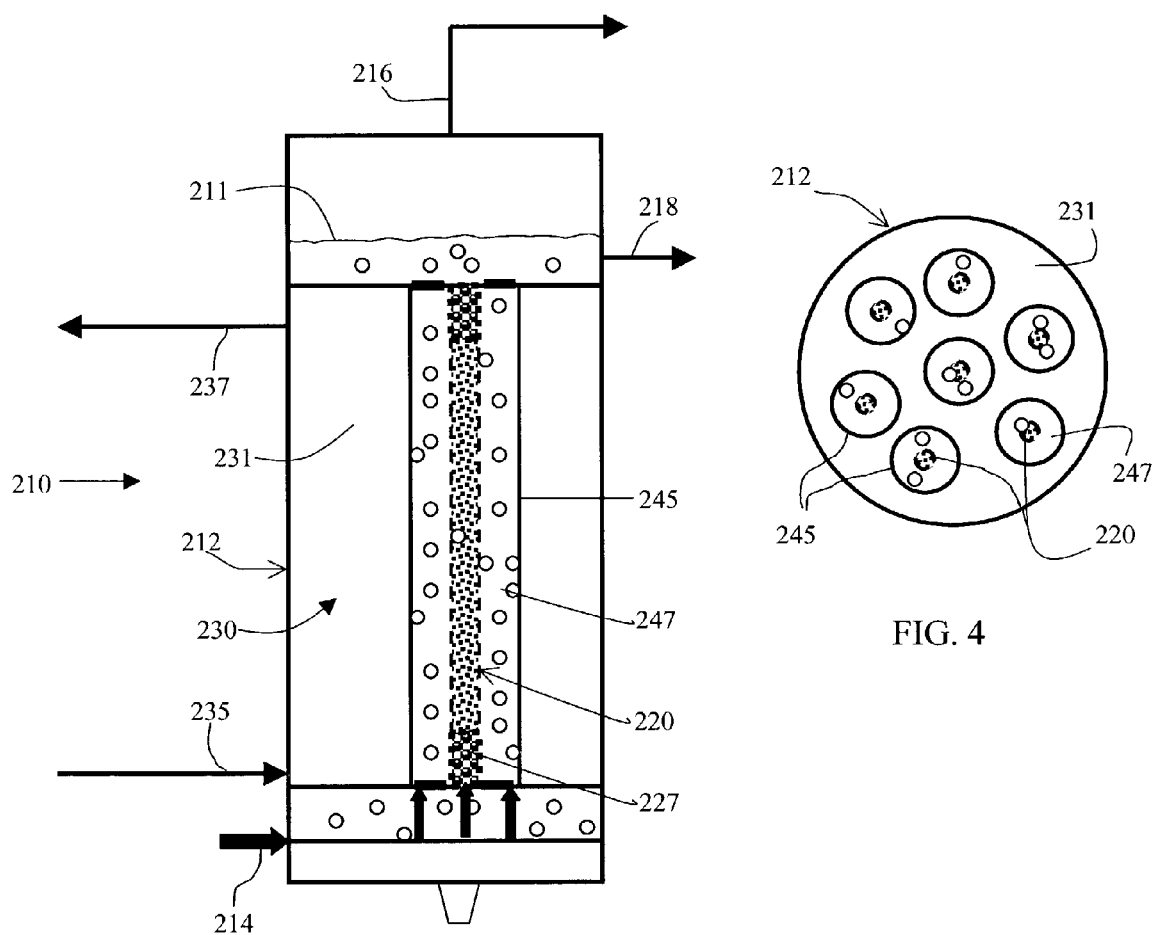
FIG. 3 is a schematic illustration of a reactor system constructed in accordance with a third embodiment of the present invention.
FIG. 4 is a cross-sectional view of a reactor system constructed in accordance with a variation of the embodiment shown in FIG. 3.

Referring now to FIG. 3, a third embodiment comprises a reactor 210 including a catalyst container 220 contained within a secondary housing 245. As above, catalyst container 220 is porous and contains the solid catalyst phase, while allowing gas and liquid to pass through. A chamber 247 is defined by each secondary housing 245 and contains gas and liquid phase 211. A second chamber 231 is defined between the outside of secondary housing(s) 245 and the reactor wall. In a preferred embodiment, a cooling medium circulates through chamber 231, forming a cooling system 230. The cooling medium preferably enters reactor 210 at inlet 235 and exits at outlet 237. The cooling medium can fill annulus 231 entirely, or can be further contained in one or more tubes (not shown). The feed gas stream enters chamber 247 via inlet 214 and diffuses into the gas and liquid phase 211. The gas reacts with the catalyst in catalyst container 220 to form hydrocarbons. Liquid products are withdrawn at outlet 218, which is located in the upper end of reactor 210, above the top end of catalyst container 220, while gaseous products are withdrawn at overhead outlet 216.

It will be understood that the configurations of either the catalyst phase or the cooling system may be modified significantly without departing from the scope of the invention. For example, in any of the embodiments described herein, the catalyst container may optionally include inert packing material 227 at either end, both ends, or throughout the catalyst phase. Inert packing 227 allows the operator to distribute the amount of catalyst throughout the reaction zone, or to separate different sections of catalyst where the catalyst may be of different formulations. Also, in some embodiments, it may be desirable to provide a gas/liquid disengaging means (not shown) in the upper end of the reactor for recovering liquid product entrapped in the gaseous phase.

Furthermore, as mentioned above, each component that is shown in schematic form in the Figures could be re-configured or duplicated without altering the operation of the system. For example, FIG. 4 is a cross-sectional view of a variation of the embodiment of FIG. 3. While the embodiment of FIG. 3 shows a single container 220 and a single secondary housing 245 within the reactor, FIG. 4 shows a reactor 212 containing a plurality of secondary housings 245, each containing at least one catalyst container 220.

Figure 5:
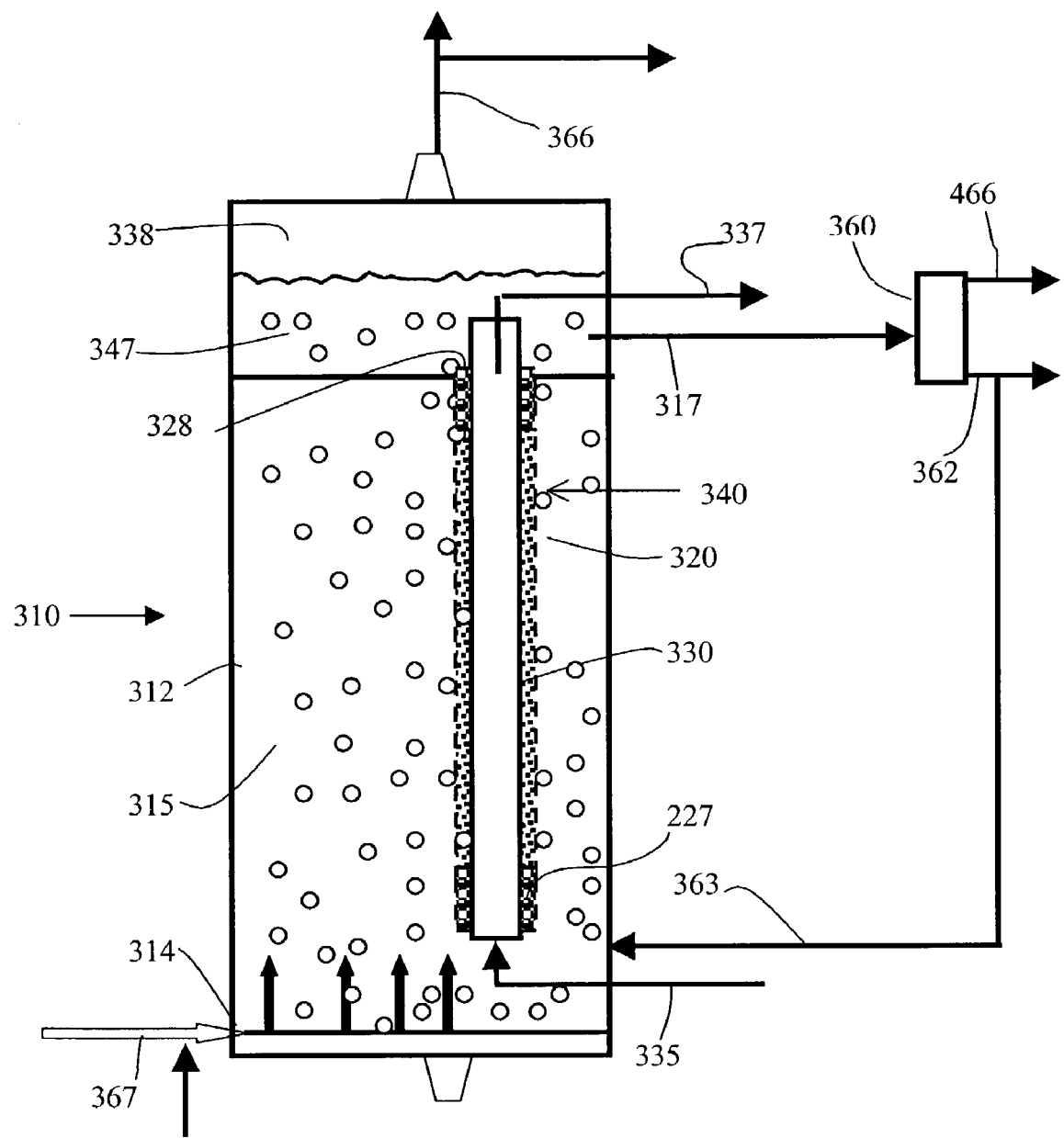
FIG. 5 is a schematic illustration of a reactor system constructed in accordance with a fourth embodiment of the present invention.

Referring now to FIG. 5, a fourth embodiment comprises a reactor 310 including a catalyst container 320 combined with a cooling system 330. As in FIG. 1, the cooling medium enters reactor 310 via inlet 335 and exits via outlet 337 and a reaction chamber 315 is defined between the outside of catalyst container 320 and the wall of reactor housing 312. As above, the gas and liquid phases occupy chamber 315. Unlike the embodiment shown in FIG. 1, a collection chamber 347 is defined directly above chamber 315 and catalyst container 320 and contains a portion of the gas and liquid phases. It should be noted that collection chamber 347 is separated from chamber 315 by a divider 327, such that fluid communication between chamber 315 and collection chamber 347 can occur only through the upper end 328 of catalyst container 320. In this embodiment, a primarily liquid stream leaves the reactor via liquid outlet 317, which is preferably positioned so as to remove liquid from collection chamber 347, and a primarily gaseous stream leaves the reactor via line 366. In one preferred embodiment, the volume of the liquid phase is such that a headspace 338 exists above the liquid in collection chamber 347.

In some embodiments, it is preferred to provide a degasser 360, which separates the gas and liquid phases into a liquid product stream 362 and a gas product stream 466. If desired, a portion of liquid product stream 362 can be recycled to the reactor via stream 363. It will be understood that a degasser can be utilized in conjunction with any of the embodiments described herein, whenever a gas/liquid separation is desired. In some instances, recycle of gaseous product streams may also be desirable.

Figure 6:
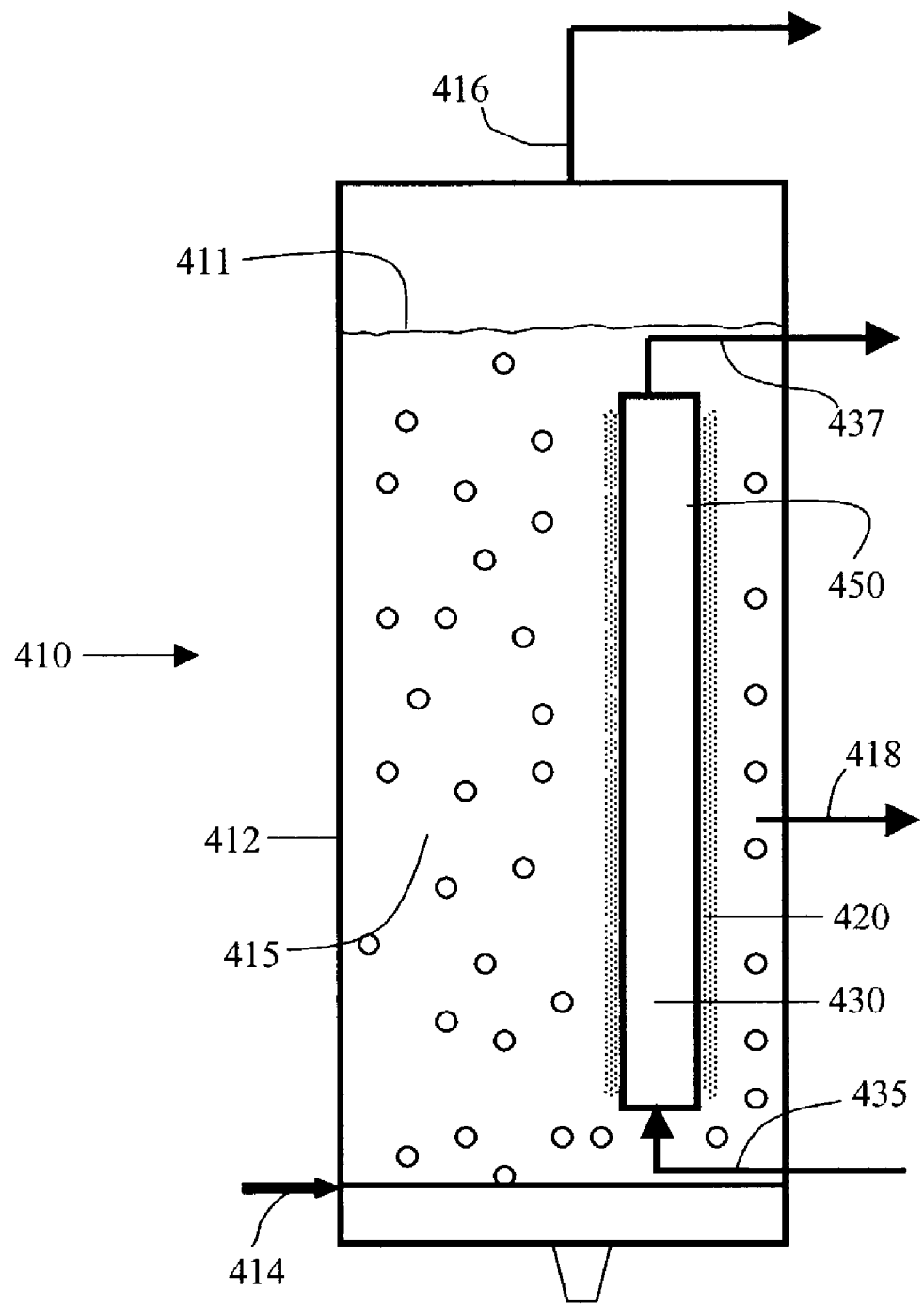
FIG. 6 is a schematic illustration of a reactor system constructed in accordance with a fifth embodiment of the present invention.

Referring now to FIG. 6, a fifth embodiment comprises a reactor 410 including a multifunctional tube 450 in a reaction chamber 415. Multifunction tube 450 preferably comprises a catalyst structure 420 and a cooling system 430. A cooling medium enters reactor 410 at inlet 435, passes through cooling system 430 and exits at outlet 437.

In a preferred embodiment, catalyst structure 420 is adhered to the outside of cooling system 430. Catalyst structure 420 may take the form of granules, particles, pellets, or a coating on a support. Regardless of its form, catalyst structure is affixed to cooling system 430 by methods known to those skilled in the art including, but not limited to, chemical bonding, physical bonding, a combination of chemical and physical bonding, or by mechanical means. By way of example only, the catalyst structure could take the form of stacked rings surrounding cooling system 30, or of granules or mesh adhered to the outside of the cooling system.

It will be understood that, in any of the embodiments described above and in any of the variations thereof, the catalyst containers and/or the cooling tubes can be placed horizontally at an inclined angle, and may be curved or straight. Similarly, it will be understood that items that are described in the singular herein can be provided in groups. For example, the system could include multiple zones comprising multiple vertical tubes, with the zones being stacked one on top of the other and separated by relatively small distances.

Likewise, the catalyst container may be packed with different catalyst compositions and/or with catalyst having different activities along its length so as to obtain very high or close to 100% conversion of the reactant gas without causing rapid deactivation of such catalysts which would be the case of a typical slurry reactor operated at high conversions.

In any of the embodiments described herein, the liquid and/or gas streams may be at least partially recycled back into the reactors. Liquid recycle can be performed with or without a liquid degassing step by methods known to those skilled in the art (i.e. via gravity circulation, with a pump, etc.). Gas recycle can be performed with or without cooling and/or partial condensation. In some embodiments, the recycled liquid and/or gas streams may be cooled before reentering the reactor. It should be noted that these recycle streams can be introduced back to the reactor at one or more locations.

In addition, it is preferred that the level of the liquid phase in each embodiment is preferably higher than the top end of the catalyst phase. Benefits realized by this arrangement include i.) improved heat exchange and ii.) lower catalyst deactivation rate. Improved heat transfer properties are achieved because the catalyst phase has a large portion of surface area exposed to the liquid phase, which absorbs heat from the catalyst phase. As a result of the high degree of mixing and gas and liquid circulation, heat generated by the catalytic reaction is transferred to the cooling system (cooling coils/tubes). A lower catalyst deactivation rate is achieved because the water concentration displays a cumulative effect along the height of the reactor, with the lowest water concentration at the lower end of the reactor and the highest water concentration at the upper end of the reactor. By providing a liquid phase level that is higher than the top end of the catalyst phase, the highest water concentration region is located above or at the top end of the catalyst phase, thereby catalyst deactivation is limited to the small amount of catalyst located in this region.

Operation

While the following discussion is presented in terms of the reactor shown in FIG. 1, it is applicable to all of the embodiments described herein, and to the principles of the present invention generally. In operation, the inside of reactor 10, and in particular the volume within catalyst container 20 is maintained at desired Fischer-Tropsch reaction-promoting conditions, such as are known in the art. A feed gas stream comprising a mixture of CO and hydrogen (syngas) enters chamber 15 via inlet 14 and diffuses into the liquid phase. As the gas contacts the catalyst in catalyst container 20 it reacts to form hydrocarbons, according to the Fischer-Tropsch mechanism. In addition, the gas agitates the liquid phase in chamber 15 thereby aiding the liquid phase in contacting the catalyst in catalyst container 20. The liquid products of the reaction (liquid hydrocarbons) are withdrawn at outlet 18 and the gaseous products (gaseous hydrocarbons) are withdrawn at overhead outlet 16. In some embodiments, at least a portion of the liquid products is recycled back into the reactor at one or more locations. Benefits of recycling the liquid products include increased mixing and therefore enhanced heat and mass transfer, which lead to better reactor performance. In addition, if the recycled liquid products are externally cooled, the cooled recycle will help to remove heat from the reactor and may improve temperature control.

As mentioned above, in one preferred embodiment gases produced in reactor 10 exit via gas outlet 16 while liquids produced in reactor 10 exit via liquid outlet 18. The gases can be sent to Fischer-Tropsch reactors in series or in parallel (with or without intermediate cooling and condensing steps), exported from the system, subjected to further separations, recycled through the Fischer-Tropsch process, and/or otherwise disposed of as desired. The gases can be recycled back to Fischer-Tropsch reactors or other reactors that produce synthesis gas. Likewise, the liquid hydrocarbons exiting via outlet 18 can be exported from the system for further processing into desired final products and/or can be partially recycled back to the reactor at one or more locations.

Referring briefly again to FIG. 5, the operation is slightly different than in other embodiments because chamber 347 contains a portion of the gas and liquid phase (not shown). In operation, the feed gas stream enters chamber 315 via inlet 314 and diffuses into the liquid phase. As the gas contacts the catalyst in catalyst phase 320, it reacts to form hydrocarbons, according to the Fischer-Tropsch mechanism, for example. Because catalyst phase 320 includes inert packing 227 at both ends, a portion of the gas and liquid phase exits chamber 315 through the inert packing 227 at catalyst phase interface 328 into chamber 347. In some embodiments, a pressure differential may be used to force a portion of the gas and liquid phase into chamber 347. As described above, the gas and liquid in chamber 347 preferably exit via outlet 317 and are fed into degasser 360, where they are separated into a liquid product stream 362 and gas product stream 366. In some embodiments, liquid product stream 362 is recycled back into reactor 310 via inlet 363 and in some embodiments, gas product stream 366 is recycled back into reactor 310 by combining it with the feed gas stream at inlet 367.

Catalyst

The present methods can be used in conjunction with any multiphase catalytic system, including any suitable Fischer-Tropsch catalyst system, oxygenate production systems, hydrogenation, unsaturated hydrocarbons production systems, hydrotreating, hydrocracking or hydroisomerization systems etc., including supported and unsupported catalysts. Since the reactor uses a stationary catalyst phase, the catalyst is not subjected to the mechanical erosion that increases catalyst attrition in slurry reactors. Hence, catalysts that are not robust enough for slurry bed reactors can be used in the present system. The catalytically active materials can include but are not limited to iron, nickel, cobalt, ruthenium, and combinations thereof, with and without one or more promoters such as manganese, vanadium, platinum, potassium, copper, ruthenium, silver, palladium and other elements, such as are known in the art. These catalysts can be supported on suitable catalyst supports, or can be provided in an unsupported form.

Feed Gases

During Fischer-Tropsch synthesis, the reactor is charged with feed gases comprising hydrogen or a hydrogen source and carbon monoxide, as is well known in the art. $H_2/CO$ (syngas) mixtures suitable as a feedstock for conversion to hydrocarbons according to the process of this invention can be obtained from light hydrocarbons such as methane by means of steam reforming, partial auto-thermal reforming, catalytic partial oxidation, or partial oxidation or a combination thereof or other processes known in the art. It is preferred that the mole ratio of hydrogen to carbon monoxide in the feed be greater than 0.5:1 (e.g., from about 0.67:1 to 2.5:1). The feed gas may also contain carbon dioxide or other compounds that are inert under Fischer-Tropsch reaction conditions, including but not limited to nitrogen, argon, or light hydrocarbons. The feed gas stream should contain a low concentration of compounds or elements that have a deleterious effect on the catalyst. The feed gas may need to be treated to ensure low concentrations of sulfur or nitrogen compounds such as hydrogen sulfide, ammonia and carbonyl sulfides.

For Fischer-Tropsch synthesis, the gas hourly space velocity (GHSV) through the reaction zone is expressed in units of volumes of gas per hour per volume of expanded bed (v/hr/v), where the numerator is the volumetric gas flow rate at standard conditions [1 atm. (101 kPa) and 0° C. (273.16 K)] and the denominator is the expanded bed volume, where the expanded bed volume is the sum of the volumes of the three phases in the reactor. In preferred embodiments, the GHSV is preferably between about 50 and about 10,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psia (552 kPa) to about 1000 psia (6895 kPa), more preferably from 80 psia (552 kPa) to about 600 psia (4137 kPa), and still more preferably, from about 140 psia (965 kPa) to about 500 psia (3447 kPa).

While the present invention has been described above in the context of a Fischer-Tropsch system, it will be understood that the devices and principles disclosed herein are equally applicable to any multiphase catalytic operation that uses a solid catalyst, including but not limited to oxygenates synthesis reactions (i.e. alcohols synthesis) and wax hydrotreating, alcohols synthesis or unsaturated hydrocarbons synthesis reactions or hydrotreating or hydrocracking or hydroisomerization of hydrocarbons or waxes. The operating parameters, catalyst and feed selection, etc. for such alternative processes will be know to those skilled in the respective arts. Likewise, one skilled in the art will recognize that the products of the Fischer-Tropsch process include but are not limited to: linear or branched saturated, unsaturated and oxygenated hydrocarbons.

While the preferred embodiments of the invention have be disclosed herein, it will be understood that various modifications can be made to the system described herein without departing from the scope of the invention. For example, the various inlet, outlet and cooling lines and the catalyst phase itself can be reconfigured, and the placement and type of feed gas inlet can be altered. Without further elaboration, it is believed that one skilled in the art can, using the description herein, utilize the present invention to its fullest extent.

What is claimed is:

1. A method for convening a gaseous and/or liquid feed to gaseous and/or liquid products using a solid catalyst; comprising:
   providing a reactor comprising a reaction chamber;
   providing a liquid phase disposed within the reaction chamber;
   providing a cooling system having a cooling element in thermal contact with the liquid phase;
   providing a stationary catalyst phase at least partially disposed in the liquid phase, wherein the stationary catalyst phase is contained in a plurality of catalyst containers, each container having an outer wall, wherein said outer wall on the container sides, top and bottom ends which is in contact with said liquid phase is porous or perforated to allow the easy passage of gas and liquid therethrough;
   providing a collection chamber disposed in the reactor above the catalyst containers, said collection chamber being isolated from said reaction chamber such that fluid flowing from the reaction chamber into said collection chamber must pass through the top end of each catalyst container;
   feeding the feed comprising a gas steam into the reaction chamber such that the gas steam agitates the liquid phase and diffuses into the liquid phase;
   contacting the feed with the stationary catalyst phase to form products;
   removing liquid products from the collection chamber of the reactor via a liquid outlet; and
   removing gaseous products from the collection chamber of the reactor via a gas outlet.

2. The method according to claim 1 wherein catalyst containers are adjacent to the cooling element.

3. The method according to claim 1 wherein the catalyst containers extend through the cooling element.

4. The method according to claim 1 wherein the cooling element extends through the catalyst containers.

5. The method according to claim 1 wherein said catalyst containers are porous.

6. The method according to claim 1 wherein said catalyst is particulate.

7. The method according to claim 1 wherein said catalyst is monolithic.

8. The method according to claim 1 wherein said catalyst is a Fischer-Tropsch catalyst.

9. The method according to claim 1 wherein the catalyst is a catalyst effective for the production of oxygenates.

10. The method according to claim 1 wherein the catalyst is a catalyst effective for the production of unsaturated hydrocarbons.

11. The method according to claim 1 wherein the catalyst is a catalyst effective for the production of oxygenates and unsaturated hydrocarbons.

12. The method according to claim 1 wherein the catalyst is selected from the group of catalysts that are effective for the reactions selected from the group consisting of hydrogenation, hydrocracking and hydroisomerization.

13. The method according to claim 1 wherein the catalyst is supported.

14. The method according to claim 1 wherein the catalyst is unsupported.

15. The method according to claim 1 wherein said cooling element comprises at least one cooling tube having a cooling medium circulating therethrough.

16. The method according to claim 15 wherein said cooling medium is water.

17. The method according to claim 15 wherein said cooling element comprises a plurality of tubes.

18. The method according to claim 1 wherein said cooling element comprises a cooling chamber surrounding said liquid phase.

19. The method according to claim 1 wherein the feed comprises synthesis gas.

20. The method according to claim 19 wherein the synthesis gas has a molar ratio of hydrogen to carbon monoxide greater than 0.5:1.

21. The method according to claim 1 further including the step of recycling at least a portion of the gaseous products into the reactor.

22. The method according to claim 21, further including the step of cooling the gaseous products prior to recycling the gaseous products back into the reactor.

23. The method according to claim 21, further including the step of at least partially condensing the gaseous products before recycling it into the reactor.

24. The method according to claim 21, further including the step of separating gaseous products from the liquid products before recycling products back into the reactor.

25. The method according to claim 21, further including the step of recycling the gas products to a reactor generating synthesis gas.

26. The method according to claim 17 wherein the cooling tubes and the catalyst containers are concentric, each catalyst container having a diameter larger than that of cooling tube to which it is concentric, so that an annulus is defined therebetween.

27. The method according to claim 1 wherein the catalyst containers have perforated walls constructed from sintered metal, woven wire mesh metal, sintered wire cloth sheets, perforated metal sheets or wedge wire type materials.

28. A method for converting a gaseous and/or liquid feed to gaseous and/or liquid products using a solid catalyst; comprising:
    providing a reactor defining a reactor volume;
    providing a liquid phase disposed within the reactor volume;
    providing a cooling system having a cooling element in thermal contact with the liquid phase;
    providing a stationary catalyst phase having a top end and being at least partially disposed in the liquid phase, wherein the level of liquid phase in said reactor is higher than the top end of the stationary catalyst phase, and further wherein the stationary catalyst phase is affixed or adhered to an outer surface of said cooling element;
    feeding the feed comprising a gas stream into the reactor volume such that the gas stream agitates the liquid phase and diffuses into the liquid phase;
    contacting the feed with the catalyst phase to form products; and
    removing the products from the reactor.

29. The method according to claim 28 wherein said cooling element comprises at least one cooling tube having a cooling medium circulating therethrough.

30. The method according to claim 28 wherein said cooling element comprises a coiled tube.

31. The method according to claim 28 wherein said cooling element comprises a plurality of tubes.

32. The method according to claim 28 wherein the catalyst is affixed to the cooling element by a method comprising chemical bonding, physical bonding or combinations thereof.

33. The method according to claim 28 wherein said catalyst is a Fischer-Tropsch catalyst.

34. The method according to claim 28 wherein the catalyst is a catalyst effective for the production of oxygenates.

35. The method according to claim 28 wherein the catalyst is a catalyst effective for the production of unsaturated hydrocarbons.

36. The method according to claim 28 wherein the catalyst is a catalyst effective for the production of oxygenates and unsaturated hydrocarbons.

37. The method according to claim 28 wherein the catalyst is selected from the group of catalysts that are effective for the reactions selected from the group consisting of hydrogenation, hydrocracking and hydroisomerization.

38. The method according to claim 1 wherein the catalyst containers are cylindrical.

39. The meted according to claim 1 wherein the outer wall of the catalyst containers comprises a tubular member.

40. The method according to claim 1 wherein the catalyst containers further comprise an inert packing material.

41. The method according to claim 1 wherein the catalyst containers are packed with different catalyst compositions.

42. The method according to claim 1 wherein each of the catalyst containers is packed with a catalyst having different activities along its length.

43. The method according to claim 1 wherein the cooling element comprises a cooling tube or multiple cooling tubes, each cooling tube passing through the reaction chamber while not directly contacting the catalyst containers.

44. The method according to claim 1 wherein a pressure differential between the reaction chamber and the collection chamber provides the fluid flow from the reaction chamber into the collection chamber.

45. A method for converting a gaseous and/or liquid feed to gaseous and/or liquid products using a solid catalyst; comprising:
    providing a reactor delimited by a reactor wall and comprising secondary housings, each secondary housing defining a reaction chamber which contains a gas phase and a liquid phase;
    providing a plurality of catalyst containers, wherein each secondary housing comprises at least one catalyst container, and further wherein each container has an outer wall on the container sides, top and bottom ends, said outer wall which is in contact with said liquid phase being porous or perforated to allow the easy passage of gas and liquid therethrough;
    providing a stationary catalyst phase disposed in said catalyst containers, in such a manner that the stationary catalyst phase is at least partially disposed in the liquid phase present in each of the secondary housings;
    providing a collection chamber disposed in the reactor above the catalyst containers, said collection chamber being isolated from the reaction chambers such that fluid flowing from the reaction chambers into said collection chamber must pass through the top end of each catalyst container;
    providing a cooling chamber defined between the outside of secondary housings and the reactor wall, wherein a cooling medium circulates therethrough;
    feeding a feed comprising a gas stream into the reaction chambers such that the gas stream agitates the liquid phase within each secondary housing and diffuses into the liquid phase;
    contacting the feed with the stationary catalyst phase to form products;
    removing liquid products from the collection chamber of the reactor via a liquid outlet; and
    removing gaseous products from the collection chamber of the reactor via a gas outlet.

46. The method according to claim 1 wherein the catalyst containers include an inert packing material at either end of the catalyst containers, both ends, or throughout the catalyst phase.

\* \* \* \* \*

UNITED STATES PATENT AND TRADEMARK OFFICE
CERTIFICATE OF CORRECTION

| | | |
|---|---|---|
| PATENT NO. | : 7,232,848 B2 | Page 1 of 1 |
| APPLICATION NO. | : 10/238008 | |
| DATED | : June 19, 2007 | |
| INVENTOR(S) | : Sergio R. Mohedas et al. | |

It is certified that error appears in the above-identified patent and that said Letters Patent is hereby corrected as shown below:

Column 9, Line 52,
Claim 1, the word "convening" should be --converting--.

Column 10, Lines 7 and 8,
Claim 1, the word "steam" should be --stream--.

Signed and Sealed this

Fourteenth Day of August, 2007

JON W. DUDAS
*Director of the United States Patent and Trademark Office*